(12) United States Patent
Olea (10) Patent No.: US 10,955,084 B2
(45) Date of Patent: Mar. 23, 2021

(54) REDUNDANT PARALLEL POSITIONING TABLE DEVICE

(71) Applicant: Huber Diffraktionstechnik GmbH & Co. KG, Rimsting (DE)

(72) Inventor: Gheorghe Olea, Bad Endorf (DE)

(73) Assignee: Huber Diffraktionstechnik GmbH & Co. KG, Rimsting (DE)

( * ) Notice: Subject to any disclaimer, the term of this patent is extended or adjusted under 35 U.S.C. 154(b) by 0 days.

(21) Appl. No.: 16/545,382

(22) Filed: Aug. 20, 2019

(65) Prior Publication Data

US 2019/0368652 A1 Dec. 5, 2019

Related U.S. Application Data

(63) Continuation-in-part of application No. 15/100,828, filed as application No. PCT/EP2014/076795 on Dec. 5, 2014, now Pat. No. 10,384,341.

(30) Foreign Application Priority Data

Dec. 6, 2013 (GB) .................................. 1321539.7

(51) Int. Cl.
| | |
|---|---|
| *F16M 11/12* | (2006.01) |
| *F16M 11/04* | (2006.01) |
| *A61B 6/04* | (2006.01) |

(52) U.S. Cl.
CPC ......... *F16M 11/121* (2013.01); *F16M 11/045* (2013.01); *F16M 11/046* (2013.01); *F16M 11/048* (2013.01); *A61B 6/0407* (2013.01)

(58) Field of Classification Search
CPC .............................. B25J 9/003; B25J 17/0266
See application file for complete search history.

(56) References Cited

U.S. PATENT DOCUMENTS

| | | | |
|---|---|---|---|
| 5,279,176 A | 4/1994 | Tahmasebi et al. | |
| 5,301,566 A | 4/1994 | Tahmasebi et al. | |
| 5,656,905 A * | 8/1997 | Tsai ..................... | B23Q 1/5462 |
| | | | 318/560 |

(Continued)

FOREIGN PATENT DOCUMENTS

| | | |
|---|---|---|
| CN | 1730235 A | 2/2006 |
| DE | 198 40 886 A1 | 3/2000 |

(Continued)

OTHER PUBLICATIONS

J. Hong et al., Transactions of the Canadian Society for Mechanical Engineering 2013, 37 (2), pp. 161-183.

(Continued)

*Primary Examiner* — David M Fenstermacher
(74) *Attorney, Agent, or Firm* — Altman & Martin; Steven K Martin (57) ABSTRACT

A positioning table device with six or fewer degrees of freedom and redundancy. Four modular legs extend from a base to a table. Each leg has three joints. In one embodiment, the bottom joint is planar and active, the middle joint is prismatic and passive, and the top joint is spherical and passive. In another embodiment, fewer than six degrees of freedom is achieved by reducing the number of degrees of freedom of selected joints. In another embodiment, the middle joint is active, and the bottom and top joints are passive.

8 Claims, 4 Drawing Sheets

(56) References Cited

U.S. PATENT DOCUMENTS

| | | | |
|---|---|---|---|
| 6,047,610 A * | 4/2000 | Stocco | B25J 17/0266 |
| | | | 74/479.01 |
| 6,330,837 B1 | 12/2001 | Charles et al. | |
| 6,382,889 B1 * | 5/2002 | Brown | B23Q 1/5406 |
| | | | 408/237 |
| 6,575,676 B2 | 6/2003 | Wang et al. | |
| 7,086,307 B2 * | 8/2006 | Gosselin | B25J 3/04 |
| | | | 74/490.05 |
| 7,124,660 B2 * | 10/2006 | Chiang | A47B 91/16 |
| | | | 74/490.05 |
| 7,172,385 B2 | 2/2007 | Khajepour et al. | |
| 8,322,250 B2 * | 12/2012 | Kim | B25J 18/00 |
| | | | 74/490.05 |
| 8,424,411 B2 * | 4/2013 | Long | B25J 9/0051 |
| | | | 74/490.05 |
| 9,536,446 B2 * | 1/2017 | Vatcher | G09B 9/12 |
| 9,579,786 B2 * | 2/2017 | Trui | F16M 11/18 |
| 10,040,151 B2 * | 8/2018 | Axinte | B25J 9/0057 |
| 10,384,341 B2 * | 8/2019 | Olea | B25J 9/003 |
| 10,406,677 B2 * | 9/2019 | Isobe | B25J 9/0009 |
| 10,414,041 B2 * | 9/2019 | Krut | B25J 9/0015 |
| 2005/0262959 A1 | 12/2005 | Angeles et al. | |
| 2009/0066100 A1 | 3/2009 | Bosscher et al. | |
| 2009/0143907 A1 | 6/2009 | Demathelin et al. | |
| 2012/0137816 A1 | 6/2012 | Carricato et al. | |
| 2014/0311271 A1 | 10/2014 | Cao et al. | |

FOREIGN PATENT DOCUMENTS

| | | |
|---|---|---|
| DE | 10 2012 008744 A1 | 11/2013 |
| FR | 2964337 A | 3/2012 |
| FR | 2965207 A | 3/2012 |
| JP | 2001121460 A | 5/2001 |
| JP | 2004 001203 A | 1/2008 |
| JP | 2010-264526 A | 11/2010 |
| JP | 2012 051054 A | 3/2012 |
| WO | 2007/055339 A1 | 5/2007 |

OTHER PUBLICATIONS

J. Feng et al., Journal of Mechanical Science and Technology 2012, 26 (1), pp. 187-194.

S. Caro et al., Proceedings of an International Symposium on the Occasion of the 25th Anniversary of the McGill University Centre for Intelligent Machines 2010, 83, pp. 341-352.

Search and Examination Report of GB1321539.7, dated Apr. 29, 2014.

Stewart, A Platform with Six Degrees of Freedom, Proc. Institution of Mechanical Eng. (UK), 1965-1966.

Gough, Contribution to Discussion of Papers on Research in Automobile Stability, Control and Tyre Performance, Proc. Auto Div. Inst. Mech. Eng, 1956-1957.

Olea et al., Precision Hexapod—Preliminary CAD (A Work for Micro), Proc. Euspen Intl. Conf.—Delft, Jun. 2010.

Brochure for type 5021 diffractometer, HUBER Diffraktionstechnik GmbH & Co. KG.

* cited by examiner

REDUNDANT PARALLEL POSITIONING TABLE DEVICE

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISK APPENDIX

Not Applicable

BACKGROUND OF THE INVENTION

1. Field of the Invention

The present invention relates to a redundant parallel positioning table device. More specifically, the present invention relates to a redundant parallel positioning table device for a precise positioning of heavy load samples, instrument and/or apparatus, e.g. in the fields and use of diffractometer machines for synchrotron facilities.

2. Description of the Related Art

Positioning systems and devices for the positioning of samples for different purposes have long been known in the prior art.

Some researches on new or existent materials are involving synchrotron X-ray tool and Diffractometers (Dm) machines to investigate the physical and/or chemical properties. To discover the intrinsic molecular and/or atomic structures and its behavior under different environmental conditions, the measurements in these large (microscopes) machines are based on diffraction technique. In order to simulate the real or virtual conditions (e.g. pressure, temperature, etc.) for a sample, the additional instruments and/or apparatus are sometimes necessary. These could weigh several tens or hundreds of kilograms and appreciable size, and the aggregates (sample & instruments/apparatus) must be manipulated in the right position towards the incoming X-ray beam. A standard experimental process includes several operations (and/or phases)—fast set ups, alignments, calibrations, go to exactly required position, keeping the pose for relative long time (e.g. hours or days) then, to restart the whole cycle for another investigation. Following these, a required positioning device should be able to perform both, simple and complex motions with enough precision and speed owing in the same time the power for carrying the relative high load and to maintain it for relative long time. Especially, it must be able to do spherical motions around a fixed arbitrary chosen point, called rotation center C (or, pivot point P) regarding the sample center, located at a distance ($d_c$) from the instrument base.

Parallel kinematic (PK) principle has been recently more and more investigated as positioning concept based on some advantages against the standard serial (stacked) principle. The most common 6 dof topology called hexapod is derived from GOUGH [V. E. Gough, Contribution to discussion of papers on research in automobile stability, control and tyre performance Proc. Auto Div. Inst. Mech. Eng, 1956-1957] and STEWART [D. Stewart, A platform with six degrees of freedom, Proc. Institution of Mechanical Eng. (UK), 1965-1966] works. The GOUGH-STEWART platform mechanism was applied for the first time as motion simulator [C. L. Klaus, Motion manipulator, U.S. Pat. No. 3,295,224, Jan. 3, 1967] and then latter as tool positioning in machine tools industry [P.C. Sheldon, Six-axis machine tool, U.S. Pat. No. 4,988,244, Jan. 29, 1991]. Actual hexapod structures for positioning (e.g. 6-SPS) are fully parallel kinematic mechanisms (PKM) composed from symmetric structures with six variable lengths actuators called struts arranged between two approximate hexagonal (or, disc) shapes—base and moving platform parts, respectively. The position (and, orientation) of the platform is resulting as a combination of strong coupled motions of linear actuated telescopic bars. The benefits are related with the increased payload, precision and dynamics, due to their intrinsic stiffer pyramidal structure. The distinctive class designed for precision positioning is called precision hexapods.

There are several proposed solutions; some of them as available products. However, when intended to be used inside of diffractometers (e.g. Dm5021/I07/DLS, HUBER GmbH Co&KG, DLS-Diamond Light Source, 107-Beamline) they are exhibiting some drawbacks in relation with the required manipulation (e.g. load: >50 kg, $d_c$=170 mm, repeatability: ±2 μm, speed: 3 mm/s) and the available Dm working space (DxA=400×420 mm, D-diameter, A-height) parameters: a) the maximum manipulated load not enough (for those fulfilling DxA, or dc), b) the rotation center point distance (dc) not inside of DxA (for all caring bigger load) and c) the workspace relative small (for both, above cases). Shortly, the hexapods volume, especially the heights are too big (or, too small) compared with the performances they offer for the allocated Dm space. In addition, the mounting surface of the platform for large instruments not always well prepared (e.g. large aperture, for cable management).

This is because the designers face with: a) the necessity to pack "inside" of the actuation struts (telescopic bars) an appreciable number of components (e.g. motor, gearhead/harmonic drive, guides, sensors, etc.); b) the shape of the workspace is resulting complex, because of the intersected number and size of the actuators; c) the undesired dynamic effects for moving motorized legs, sometimes appreciable, affecting the maximum speed. And, the singularities (and, collisions) occurred must be detected and avoided for precision tasks; however, difficult to be done, as is direct related with the numbers of joints and components. Finally, the simple motions: translation-X,Y,Z (and/or rotations-Rx,Ry,Rz) are difficult to be predicted by non-parallel kinematic expert staff, when simple and fast alignment operations are to be done in the experimental rooms.

Other architectures have been investigated during the time for precision 6 dof positioning tasks.

The U.S. Pat. No. 5,301,566 relates to a six degree-of-freedom parallel-(mini)manipulator having three inextensible limbs for manipulating a platform attached via three non-collinear universal joints and two-degree-of-freedom parallel drivers. By using the minimum number of actuated and supporting points, and bidirectional planar motors an increased workspace, stiffness and accuracy compared with Stewart/Gough mechanism have been claimed, beside of other advantages e.g. (direct kinematics, few components, etc.). However, the static and dynamic characteristics are very much depending of the number of components (three) being one axis symmetric arranged, only.

There are also several proposals for PK mechanisms working as positioning table devices. PCT publication No. WO2007/055339A1 describes a three-dimensional positioning table (rectangular shape) which has the ability to perform high-precision motions, as a result of combined actions of mainly two separated positioning devices. An elevating (Z) and a table plate (XYRz/PKM) devices are both connected through a planar bearing support plate and three vertical linear guides. The elevation device is including a stage system of two guided wedges which in their relative motions against a fixed support produced the lifting/down of the platform. However, these combined hybrid parallel-serial structures cannot provide whole motion capabilities spectrum (6 dof). The Japanese patent publication No. JP2012-51054A describes a positioning table which is using three mobile supports, each of them providing a lifting/down motion through a combination of three linear guided parts on which on one, the motor is attached; and, on the second a spherical bearing. A load in space (3 dof) is positioned with this tripod architecture through several moving parts and guiding means supposing to affect the general stiffness.

Redundancy is a relative new concept applied to parallel kinematic mechanisms. It increases the mechanisms capabilities of stiffness, working space, accuracy and speed for both, spatial and planar structures. Two concepts have been studied until now—the kinematic redundancy (adding a chain/leg) and the actuation redundancy (adding an active joint), respectively. The redundancy has also the advantage of avoiding singularities and to work in difficult conditions when one or more actuators are falling. However, few manipulation and/or positioning products have been released until now.

The Japanese patent publication No. JP2010-264526A relates to a redundant spatial parallel mechanism using four pairs of two actuators having one dof each. The architecture is similar with hexapod ones based on strut actuators but with special designed interconnected joints at the top end. In order to perform the required motion task, the control function must take into account only six suitable selected active struts. The resulting height (high) of the device related upon the actuators lengths is similar as in the hexapods case one.

The French patent application No. FR2965207A1 describes a redundant parallel robot having six degrees of freedom. The mechanism can be seen as comprising four articulated kinematic closed chains each with two dof actuation from the base. A main serial chain is supported from other through a rotational joint and then it is connected to the platform through separated rotational joints including a pivotal one. The pairs of actuators are located alongside of a quadrilateral shape moving the platform and acting around the corners. The parallel type singularities are avoided. And, by using rotational motors and arms (bars) high workspaces and dexterity manipulation tasks could be delivered, but not together with precision because the stiffness is not at its best. Improved values perhaps are obtained in the embodiment using vertical linear actuators (FR2964337A1), but the platform size is still supposed to be much smaller than the base is.

The Chinese patent No. CN1730235A relates to a redundant parallel mechanism with six degrees of freedom used as a structure for machine tool in order to increase its axial rigidity and workspace, by using four telescopic legs, each of them moving around a ring base through revolving pairs as part of their sliding blocks. The circular guides realize a large range of rotational movement and increase the attitude space, but the active joints are interposed between passive ones diminishing the maximum stiffness.

All these devices described above have the capability to partially (less than 6 degrees of freedom) or fully (6 degrees of freedom) pose a body in space using either non-redundant (e.g. parallel or hybrid) or redundant (e.g. parallel) structures. However, none of the above devices is perfectly suitable for specific synchrotron related diffractometer applications.

BRIEF SUMMARY OF THE INVENTION

The present invention provides a 6 or fewer degrees of freedom positioning device with superior performance and capabilities by being more adapted to the scope compared with devices of the current art.

An object of the present invention is to provide a positioning table with an increased size (including the aperture) and adequate shape (flat) supporting and fixing surface for carry the specific diffractometers loads. Another object is to provide a table which can accommodate the most demanding tight space requirements by being more compact (e.g., having a lower profile). Another object is to provide a positioning table with increased precision, including stability. Another object is to provide a device with increased speed. Another object is to provide a method to intuitively perform simple Cartesian motions (e.g., translations and/or rotations) automatically or manually.

BRIEF DESCRIPTION OF THE DRAWINGS

For a fuller understanding of the nature and object of the present invention, reference is made to the accompanying drawings, wherein.

DETAILED DESCRIPTION OF THE INVENTION

The present application is a continuation-in-part of U.S. patent application Ser. No. 15/100,828, which is a national stage application of PCT application No. PCT/EP2014/076795, both hereby incorporated by reference in their entireties, on which this application is based.

The inventor of the present invention has surprisingly found that the devices according to the following aspects of the present invention provide a solution to the above described objects of the present invention and additionally provide technical effects and advantages which were unexpected and surprising in view of the prior art. These technical effects and advantages will be explained and are apparent from the examples accompanying this disclosure.

In a first aspect, there is provided a parallel positioning table device (Rd-PPT) comprising a stationary base (B) and a moveable table (T). The parallel positioning table device can be a redundant parallel positioning device table. The moveable table can be moved relative to the stationary base in all six-degrees-of-freedom (6 dof). The moveable table can have a fixing surface ($\Sigma_T$). The fixing service can be a fixing surface whereupon a sample (Sp) or related bodies (Bo) for investigations can be mounted on. At least one set of four supporting legs may be symmetrically and in pairs arranged around a center of the base connected with one end to the stationary base and with another end to the movable table. One of the supporting legs can be redundant. All of the supporting legs can be 213 kinematics chains (K). Within the context of the present disclosure, redundant refers to any positioning table device having at least one set of four supporting legs, wherein at least one supporting leg is redundant in view of the other legs.

In a preferred implementation of the present invention, the parallel positioning table device can be modular. Within the context of the present disclosure, modular means that the table device comprises the stationary base, the moveable table and the supporting legs in a modular manner. The supporting legs can be provided as positioning modules (Pm). The positioning modules can be arranged vertically and parallel with respect to one axis of symmetry (Z) and orthogonal with respect to a second axis of symmetry (X/Y), preferably as active 2 dof pillars.

Each of the positioning modules can be a stacked combination of one active Ac—planar driven and two non-active, El—inclined elevation and Gu—spherical guiding positioning units (Pu), from which the first two (Ac, El) can be compact parallelepiped blocks with the same base shape and size.

Additionally, an active positioning unit Ac can be a 2 dof in-parallel actuation A unit. The actuation (A) unit may comprise four orthogonal motion axes, wherein along two of them—adjacent ones, are acting a set of two linear actuation main parts (A11, A12), another (A'11, A'12) being redundant, perpendicularly on the sides of a common mover (M) with planar guiding surface ($\Sigma_1$).

In a preferred implementation, the parallel positioning table device's elevation positioning unit (El) can comprise a pair of parallel wedges (W) with V-type adjustable inclined guiding surfaces ($\Sigma_{21}$, $\Sigma_{22}$). The lower part (W1) of the guiding surfaces ($\Sigma_{21}$, $\Sigma_{22}$) may be fixed on the actuation (A) and the upper part (W2) may be supporting the spherical (S) positioning units, forming a V-type shape with the opposite leg of a (El) positioning unit.

A guiding positioning unit (Gu) may be a compact spherical joint (S). The compact spherical joint (S) can have convex-concave spherical shapes in contact with adjustable ($\Sigma_{31}$, $\Sigma_{32}$) surfaces. A first part can be a truncated conical pillar p with a precision calibration sphere (S) at one end. Another perpendicularly mounted on the upper side of the elevation (Pu) housing the interconnected (H1, H2) parts integrated in the bottom side of the table.

In a preferred implementation, all four planar 2P joints may be mounted in pairs (2×2P) on the stationary base having orthogonal axis each other (P1P3/P2P4) and substantially parallel to the stationary base surface ($\Sigma_B$) forming a coplanar actuation module (Am), as part of a 6-4-(2P)PS parallel kinematic mechanism, with only linear and spherical joints, respectively and passive joints (P) being all inclined with the same angle ($\alpha$).

The positioning modules (Pm) can be located in the middle sides, or in the corners of a stationary base square and/or movable table in terms of a central aperture (D).

In another aspect of the invention there is provided a use of the redundant parallel positioning table according to the first aspect of the disclosure to generate simple Cartesian spatial: translations—TX or TY or TZ and rotations—RX or RY or RZ motions and linear—X or Y or Z and angular—$\alpha X$ or $\alpha Y$ or $\alpha Z$ displacements, as direct involvement of motions with equal, or equivalent displacements, by using all or only some of the corresponding active axes linear motions (tx,ty) and displacements (X,Y).

In a third aspect the present invention relates to a redundant parallel positioning table device. The redundant parallel positioning table device may comprise a stationary base and a moveable table. The moveable table may be moved relative to the stationary base in all six-degrees-of-freedom. The movable table may have a fixing surface upon which a sample or related instruments for investigations can be mounted on. Preferably, at least one set of four supporting legs are symmetrically arranged around a center of the base connected with one end to the base and other end to the movable table.

Ideally, the table positioning device may be conceived to be modular and has the supporting legs as positioning modules vertically in-parallel arranged in respect with one axis of symmetry and orthogonal in-pairs in respect with other of their axis of symmetry.

Each of the positioning modules may be a pre-determinate combination of one active and two non-active positioning units.

The table positioning device may additionally comprise two degrees of freedom in-parallel actuation components with at least two orthogonal motion axis each and a planar guiding surface.

In a preferred implementation, the table positioning device additionally comprises an elevation component based on an inclined guiding surface of which the first said bottom part is fixed on the actuation and the second part said upper is supporting the guiding unit forming a V-type shape with the opposite component from a pair.

The table positioning device may additionally comprise a guiding component with a convex-concave surface connecting the upper side of the elevation component with the bottom side of the table.

All of the active positioning units may be mounted on a planar base and in-pairs, being orthogonal each other and both substantially parallel with the base surface.

On each of the elevation units may be perpendicularly mounted guiding positioning units able to permit orientation motions and displacements for the positioning modules and by their combined work, the entire table device to be translated and/or oriented.

By choosing only part of actuation axis, a positioning device with fewer than 6 dof can also be made.

In a fourth aspect of the present invention there is provided a basic methodology for generating spatial motions and displacements as combination sequences of all or some of the active translational motions and/or displacements generated by the table positioning device according to the third aspect of the present invention.

The invention will now be further illustrated by way of working examples. It is to be understood that these working examples will not limit the scope of the protection of the present invention and are intended and presented for illustrative purposes only.

The followings notations are being used:

| Type | Kinematics/Geometry |
| --- | --- |
| $A_i$, A | Guiding, center platform points |
| $B_i$, $B_{i0}$ | Actuation, fixed base points |
| $C_i$, C, | Sliding points, rotation center |
| $a_i$, $b_i$ | Guiding, actuation points distance |
| $q_i$ | Generalized (actuated) coordinates |
| J | Joint |
| Dof, dof, (f) | Degrees-of-freedom (joints) |
| K | Kinematic chain |
| P, $(Pl)_2$, S | Prismatic, planar (2dof), Spherical Joints |

-continued

| | |
|---|---|
| R(Rx, Ry, Rz) | Rotational motion |
| T(XYZ) | Translational motion (Displacement) |
| (Σ), (C) | Surface, curve |
| d | Distance |
| l | Links |
| I, . . . , IV | Kinematic levels |
| 1, 2, 3, 4 | Actuated joints motion |
| i, j = 1, . . . , 4 | Index (number of points, chains, etc.) |

| Type | Design/Drawings |
|---|---|
| Ac, (A) | Actuators |
| B, (Bo) | Base, body (e.g., instrument) |
| El | Elevation unit |
| F | Fixing means (e.g., screw) |
| Gu, g | Guiding unit, means |
| H | Housing |
| L, l | Lengths |
| M (m) | Mover (motor) |
| Pm (Pu) | Positioning module (unit) |
| p | Pillar |
| r, D | Radius, diameter |
| S, s | Spherical (joint), Sphere |
| Sp | Sample |
| T | Table |
| W | Wedge |
| α, β, γ, ψ, φ, θ | Angle/angular motion (displacements) |
| ⊥, ∥ | Perpendicular, parallel (ax) |

The architecture of a positioning device is an important factor regarding its capabilities. The chosen structure, kinematics, geometry, and optimum design affect the required final static, kinematic and dynamic parameters.

Figure 1:
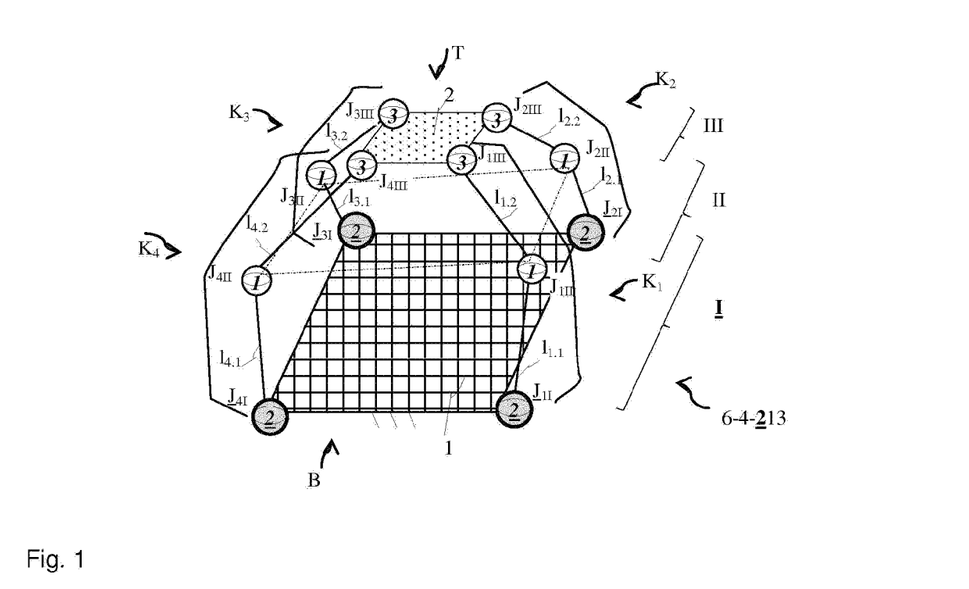
FIG. 1 represents the 6-4-213 topological concept of the redundant parallel positioning table device.

The graphical representation of a structure working as a positioning table device is proposed in FIG. 1. The topological kinematic concept is fundamentally based on two rigid bodies (or, elements)—a first element (1) called the base (B), generally fixed to the ground, and the second element (2) supposed to move called platform, or table (T). Both of them are connected by four identical kinematic chains or, legs ($K_i$), i=1, . . . , 4—a succession of mobile rigid pairs of links ($1_{i.1}$, $1_{i.2}$) and triplets of joints ($J_{i,j}$) arranged on three levels (j=I, . . . , III) in the same succession regarding joints' dof ($f_{ij}$=213) starting from the primary element (1). All joints at the first level (I) situated on the base are called actuated or active joints. ($J_{iI}$) are actuated (bold and underlined noted), whereas the remaining joints situated on levels two (II) and three (III) are non-actuated or passive joints ($J_{iII}$, $J_{iIII}$). By this symmetric structural arrangement, the total degrees of freedom or mobility (M) of the mechanism computed with Kuzbach-Grübler formula: $M=6n-\Sigma_i^j (6-f_i)$ for spatial mechanisms is resulting as six (M=6), because moving parts n=9, number of joints j=12 and their degrees of freedom $f_i$=2,1 and 3, (j=1 . . . 4, 5 . . . 8, 9 . . . 12). The result qualifies the kinematic mechanism (6-4-213) as having full spatial mobility, however, obtained with the price of redundancy. The degree of redundancy comes from one chain addition ($Rd_K$=1) and the actuators number ($Rd_A$=2). In fact, the above graph represents not only one type of the mechanism's topology, but an entire QUATTROPOD's (QP) 6 dof redundant PM family. Each member depends on particular choice of joints, e.g. 1-P (Prismatic), 2-PR (R-Rotation) 3-S(Spherical). These particular very symmetric, over actuated, and over-constrained members are able to perform heavy load stable motions with increased static and dynamic capabilities because of supplementary contact/acting points and power compared with three legs (a tripod), being in the same time more versatile than six points (hexapod) structures.

Figure 2:
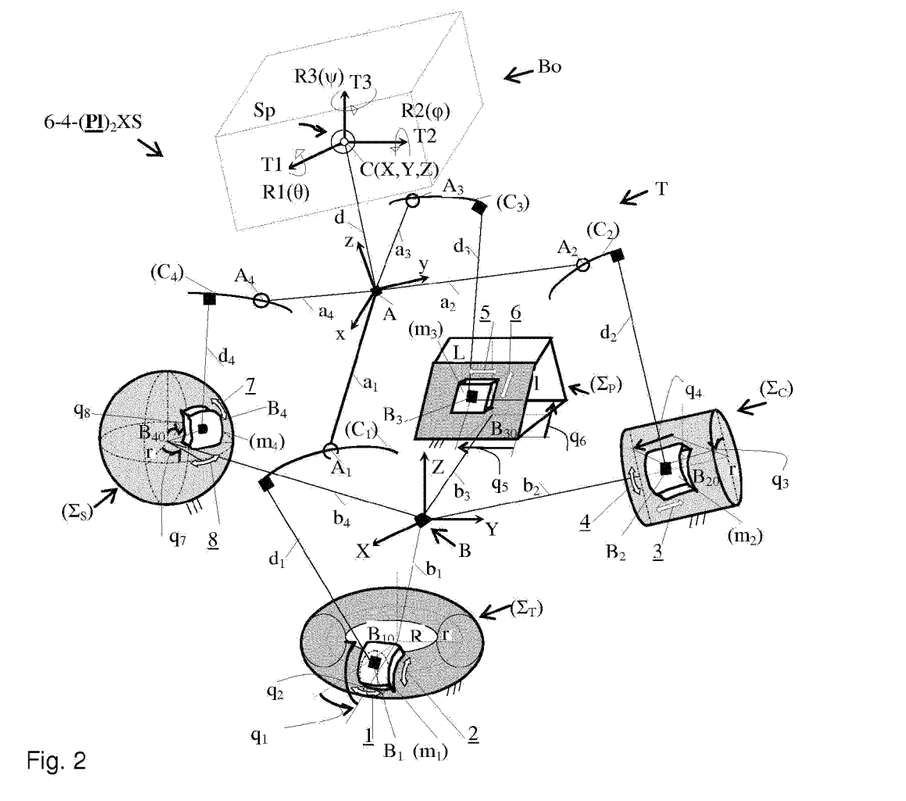
FIG. 2 represents the 6-4-$(P1)_2XS$ general kinematic model for redundant parallel positioning table device.

A general kinematic model helps to define a particular mechanism based on the actual existing (or developed) portfolio of kinematic joints and their general reciprocal arrangements. It is useful also to formulate the methodology of establishing the input/output (closure) equations. The above 6-4-213 graph permits to freely choose the actuated and non-actuated type of joints as: 1 dof as linear (P), rotation (R), or helicoidal (H); 2 dof as (PP), (PR), or (RR); and 3 dof as spherical (S), (UR), or (RRR) joints. A couple of active 2 dof joints based on surface/mover principle could be used having—planar ($\Sigma_P$), spherical ($\Sigma_S$), cylindrical ($\Sigma_C$), or toroidal ($\Sigma_T$) fixed surfaces, on which the linear or curvilinear pathways motions (1, . . . , 8) of the sliders are moving accordingly, as shown in FIG. 2, representing 2P, $2R_S$, PR, and $2R_T$ driving joints. Through their simultaneously or separated combined actions, each of the surface movers ($m_1$, . . . , $m_4$) or acting points $B_i$ ($X_{Bi}$, $Y_{Bi}$, $Z_{Bi}$, i=1, . . . , 4) defined by pairs of mechanisms' curvilinear generalized coordinates ($q_i$, $q_{i+1}$), i=1, . . . , 4 are changing the spherical joints (S) center $A_i$ ($X_i$, $Y_i$, $Z_i$, i=1, . . . , 4) positions, which in turn, moves the attached sample (Sp) and instrument body (Bo) generally in three spatial translational and/or rotational directions (3T/3R). In other words, $A_i$ points are moving on curves ($C_i$), i=1, . . . , 4 each having 2 dof ($l_i$—curvilinear coordinate variable, see also FIG. 3). Following this, the resultant pose—positions (XYZ) and orientation (ψ, φ, θ) values, respectively, of manipulated objects depends on: a) the actuation displacements ($q_i$, i=1, . . . , 8) and b) geometrical ($a_i$, $b_i$, li, $d_i$, L, 1, R, r) parameter values for a general case of a 6-4-$(Pl)_2XS$ mechanisms (X—undefined 1 dof, $(Pl)_2$—generalized curvilinear planar 2 dof joints). Compact Spherical (S) joints are given a simplification in to formulate and solve the motion (position) equation. In this context, the ($C_i$) and $A_i$ are called guiding curves and guided points, respectively. The closure equations can be easy derived by expressing their coordinates in both Cartesian systems—fixed (B-XYZ) and mobile (A-xyz); the input (or, output) parameters (X, Y, Z, ψ, φ, θ and $q_i$) are implicitly included.

Figure 3:
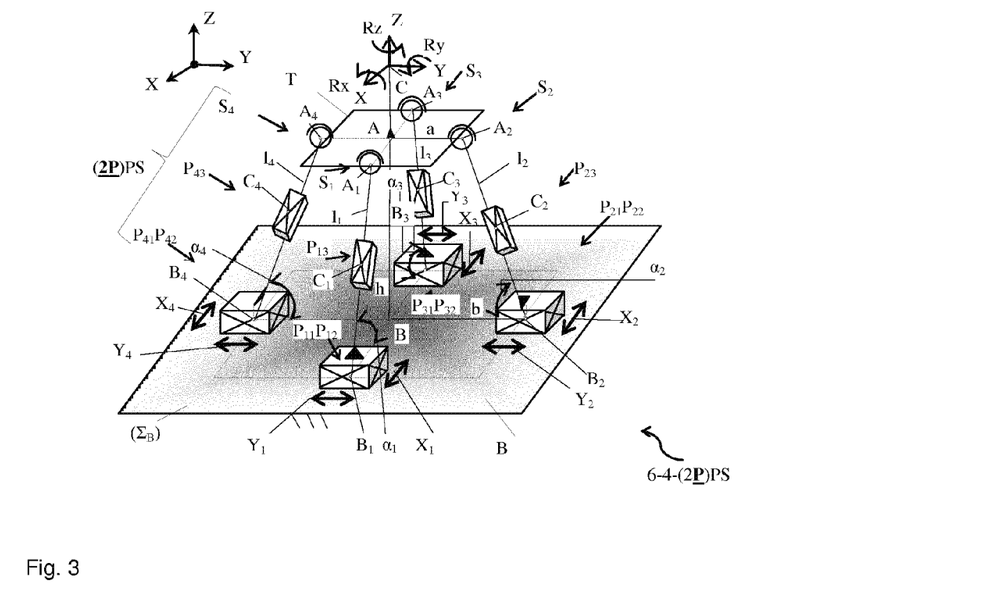
FIG. 3 represents the kinematic model of 6-4-(2P)PS mechanism for redundant parallel positioning table device.

A kinematics scheme helps to understand the working behavior of a mechanism and to formulate the motion equations. The positioning related problems (direct/inverse) are then solved based on the input/output displacements and geometric parameters. A parallel mechanisms kinematics for a positioning table based on above 6-4-$(Pl)_2XS$ model is represented in FIG. 3. It is consisting from a symmetric arrangement in-pairs of four identical $(Pl)_2XS$, i=1, . . . , 4, open kinematic chains, each comprising one planar actuated joint (2P) and two—prismatic (P) and spherical (S) non-actuated joints linking a quadrilateral platform-like table (T) with the base (B) of the same shape. The (2P) joints provide 2 dof in a plane located on substantially a planar base surface ($\Sigma_B$). Each of the opposite actuated joints ($2P_1, 2P_3/2P_2, 2P_4$) being symmetrically arranged, have all their linear motion axis orthogonally to each other (e.g., $P_{11} \perp P_{12}$, etc.) and subsequently orthogonally with other joints axis ($P_{11} \perp P_{22} \perp P_{33} \perp P_{44}$) This symmetric combination of actuated axis forms a general 4×2P planar Actuation module ($A_m$), providing a simple and direct way for moving the table along each of the horizontal Cartesian planar axes—X($X_1, X_2, X_3, X_4$) and Y($Y_1, Y_2, Y_3, Y_4$), respectively. Non-actuated opposite prismatic joints pairs ($P_{13}P_{33}/P_{23}P_{43}$) all have identical inclined angles ($\alpha_i$, i=1, . . . , 4) with respect to one of the actuated axis. By the two sets of in-pair actuators motion through simultaneously and concurrent displacements, the platform moves in an orthogonal direction (Z) to the previously ones (X and Y) based on a V-type kinematics principle. The inclined angles can be any from 0 to Π (except Π/2) radians; in figure α<Π/2. By simultaneously and motions of pairs of actuated joints in the directions not related to the axis of rotation, or in other words, orthogonally on rotation axis location, the result is the rotations around one of the planar orthogonal axis (e.g.—$X_1,X_3$/Ry); the same procedure applied for Rx($-Y_2,Y_4$). The third rotational motion (Rz) is obtained by the action of all four (2P) joints in the same direction of rotation (and, in the same time)—e.g., Rz/($-X_1,Y_1/-X_2,Y_2/X_3,-Y_3/X_4,-Y_4$). Through this specific arrangement 6-4-(2Pl)PS (or, 6-4-(PP)PS), a device can do some of the simple translational or rotational motions along or around tri-orthogonal directions very easily and intuitively through decoupled motor motions, which greatly simplifies its control. As is fundamentally stated everywhere, the minimum number of points to position a body in space is three, however in this over-constrained, but over-actuated parallel mechanism, the fourth actuator is acting as a means for increasing the kinematics (speed/acceleration) and/or dynamic (inertia) capabilities, beside of an evident fundamental static stability. Moreover, if damage occurs somehow in a motion axis, the remaining ones could support the work until repaired. Note: The entire kinematics of the mechanism is built on using two types—linear and spherical joints, only. This small diversity could reduce the total manufacturing costs.

Figure 4:
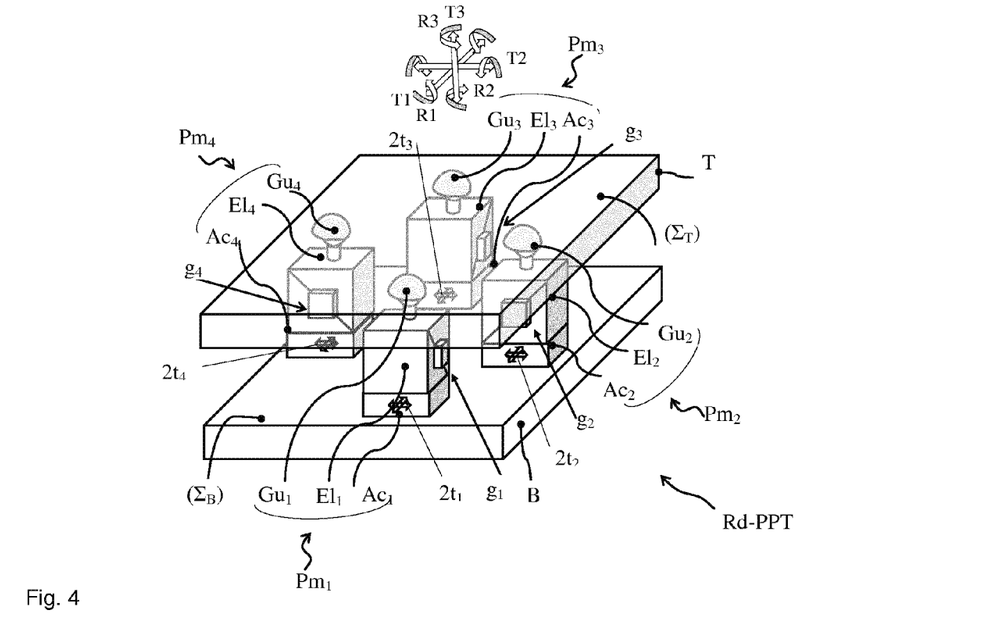
FIG. 4 is a 3D view of the redundant parallel positioning table device design concept.

A good way to materialize the kinematic principle is a key factor to fulfill the required static, kinematic and/or dynamic performances. In FIG. 4, a general design concept is proposed based on 6-4-(2P)PS mechanism kinematic model. Redundant Parallel Positioning Table (Rd-PPT) design consists from a set of four active Positioning Modules ($Pm_i$, i=1, . . . , 4) arranged on a substantially planar base surface ($\Sigma_B$) and supporting a platform-like table (T) both having polygonal (quadrilateral) shapes. Each of the Positioning Modules (Pm) comprises two types of Positioning units ($Pu_i$, i=1,2) in respect with their participation at the general motion; the first ones are called actuated and the second ones non-actuated (passive). The Actuation ($Ac_i$), i=1, . . . , 4 Pu are driving means providing 2 dof planar motion activated by any of the actual or further developed linear bidirectional motorized drivers, as direct driven (DD), e.g., planar motors, coming from each or combination of stepping, servo, magnetically or piezo effects, or including in-parallel or serial or hybrid (parallel-serial/serial-parallel) electromechanical actuation principles, or standard (motor-gearhead-motion screw-guides) solution. The last one, in the case of an XY stage provides high stability of motion over time, however, not very much to be preferred, because of cable management difficulties and the resulted reciprocal errors (e.g. perpendicularity, etc.) with the direct effect on precision. (Note: DD means driving the load directly without any transmission mechanism, such as pulleys, timing belts, ball screws and gears enabling both, high-precision and high-speed positioning. For long strokes, they have to rely on advanced servo technology to ensure high stability.)

The second types of Pu include the Elevation (El) and Guiding (Gu) means, respectively.

The ($El_i$) units are based on planar wedge motion principle consisting from two—lower, fixed on ($Ac_i$) and upper, supporting ($Gu_i$) parts having reciprocal inclined planar surfaces of motion and auxiliary guiding means ($g_i$). By their relative motion, and following the result of the combined actuated unit(s) motions, the upper part moves up and down constrained by the distance of two opposite ($Pm_i$). For heavy loads and precision motions, the simple way of materializing them is to have flat sliding surfaces. However, others contact surfaces, as rolling/rolled (rails) or fluid (air, liquid) based principles can be also taken into consideration if fit with the final required performances.

The Guiding (Gui) Pu are based on spherical motion principles and consist at least two parts—lower, fixed on upper part of ($El_i$) and upper, supporting and giving the opportunity the table (T) to be oriented in 3D. The relative motion of the above parts involves a spherical guiding surface in order for the table (T) to perform the required rotational motions. The type can be any from compact—rolling, sliding spherical joints (S) principle or even separated—simple rotations joints (RRR) and combination of them (UR/RU) design. Other functional principle, as air or any fluid can be also taken into consideration depending on the applications.

Figure 5:
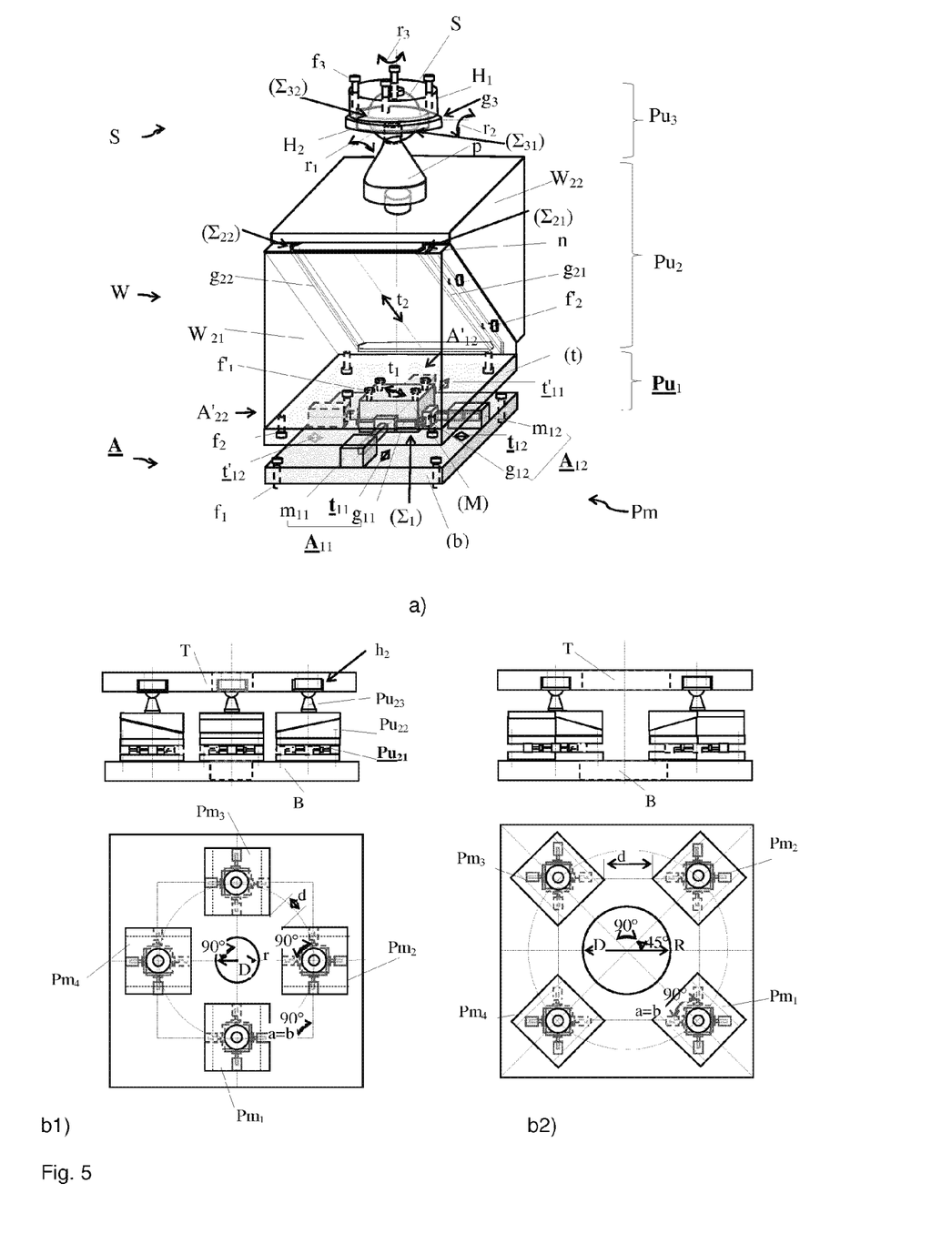
FIG. 5 is an example of a Positioning module (Pm) and two assembly embodiments.

The optimum design including the size and type of components are affecting not only the final performances but the entire characteristics and life of the device. In FIG. 5, a Positioning module (Pm) embodiment and two particular arrangements for whole devices are shown. The (Pm) is based on a stacked combination of three basic Positioning units ($Pu_i$, i=1,2,3): a) first one ($Pu_1$)—active/actuated (A) and b) second ($Pu_2$) and third ($Pu_3$) inactive (passive)—wedge (W) and Spherical Joint (S) types, respectively.

The (A) Pu is based on in-parallel actuation principle, consisting from in principle a square shape base (b) on which a pair of two similar linear actuation units ($A_{11},A_{12}$) having each of the motion axis ($t_1,t_2$) orthogonal each other is moving in principle a rectangular mover (M) solidary being with a table (t) of the in principle same shape with (b) and fixed through several (at least four) fixing ($f_1$,) and centered (e.g., pin, at least one) means. In addition, the (t) has in principle a flat surface supporting the next Pu (W). Each of the single actuation units ($A_{11}$) and ($A_{12}$) is comprised preferably of a linear actuated motor ($m_{11}$), and ($m_{12}$) with a part fixed on the base and other (pusher) moving free and having a perpendicular and coplanar guide assembly ($g_1,g_2$) at one end with one part (preferable, the rail) fixed on (M). By pushing (or, pulling) the ($A_{11}$) or ($A_{12}$), the (M) is forced to move in and along each of the orthogonal directions ($t_{11}$ or $t_{12}$), but more specific in a (general) planar motion ($t_1$) through their combined action. This orthogonal actuation unit (A) could be developed further, by enforcing its power through the addition of another preferably orthogonal actuation unit A'($A'_{11},A'_{12}$). By this, each of the simple main actuation units are working in tandem with the additional ones ($A_{11}$, $A'_{11}/A_{12}$, $A'_{12}$) to perform heavy duty motion cycles by the full working of all four (4) actuators or helping as partial work, in the case of working only three (3), for example. This complete new actuation unit (A, A') is fitting even better with the square base (b) and table (t) shape forming a strong and compact well balanced powered unit, if necessary. There is no particular limitation in the specific uses of several other in-parallel linear actuators number, as for example three, five, etc., and the corresponding base/table polygonal shape accordingly. However, the two is the minimum. In principle, the guiding means ($g_{11},g_{12}$) is preferably from sliding principle, but could be any other, e.g., rolling, magnetic, etc., as well. This at the base in-parallel actuation solution, beside the advantage of being able to provide no moving cable solution with direct effect on increased precision may use specific heavy load guiding means for the mover (M), e.g., 2 dof planar bearings ($\Sigma_1$). And, in the case of more than two actuators is opening the way to choose smaller size motors and components for a more compact low-profile actuation module inside of the same power parameters as two units. In all cases sensors may be used for more accurate motion.

The $Pu_2$ unit consists of a wedge (W) assembly—a fixed lower part ($W_{21}$) and movable upper part ($W_{22}$) which in principle, is having the same support shape surface as similar to that of the table (t) A unit.

By the relative motion of this pair, through the specific guiding means ($g_{21}, g_{22}$) with V groove profile surfaces ($\Sigma_{21}, \Sigma_{22}$), the upper part can be precisely adjusted for smooth and accurate motion against lower one through a flexible nervure (n) sliced along one of the sliding guides ($g_{21}, g_{22}$) and fixed then with several (at least two) fixing means ($f_2$), e.g., screws. The ($g_{21}, g_{22}$) guides could have any another form which fit the scope, e.g., angular or even other means for performing the translational resulted motion ($t_2$), based on rolling principle e.g. balls, cross-roller rails and carriages; or, for more precise motion requirements, the air guides.

The Pu3 is the Spherical joint (S) positioning unit preferably comprising a sphere (s), e.g., calibration ball manufactured for metrological purpose with small roundness errors encapsulated (but, moving) in two houses ($H_1$, $H_2$) with reciprocal concave surfaces ($\Sigma_{31}$, $\Sigma_{32}$), and supported by a truncated conic pillar (p). ($H_1$) is holding ($H_2$) and it has an external guiding surface (g) for precise and smooth assembly with the table (T) using several (at least four) screws fixing means ($f_3$). The ($H_1$) and ($H_2$) are adjustable to permit the smooth rotation of the convex-concave spheres with the center substantially coaxial; the conical pillar support axis is perpendicularly mounted in principle on the planar support surface of upper wedge ($W_{22}$). Between the relative motions of the three surfaces the sliding contact principle is preferable to exist. Two preferred embodiments using above ($Pm_i$) as parts of entire parallel table positioning device assemblies are shown in FIG. 5b. The embodiments consist in using the preferably identical four modules (Pm) from above coupled in pairs ($Pm_1, Pm_3/Pm_2, Pm_4$) being in a circumferential and equidistant way arranged around a common vertical axis of symmetry of both, the base and table with the same square shapes size (a=b). The actuation/supporting legs axis of symmetry are intersecting: a) the middle-points, FIG. 5b1 and b) the corners, FIG. 5b2 of the actuation (b)/supporting (a) square, respectively. The rigid base (B) in both cases is expected to be a flat surface (plate) attached direct to a more generally flat surface of the machine basic structure (diffractometer); or, through additional device (e.g. gonio stages). Note, the base and the flat table could have also various planar polygonal shapes beside the square one, e.g. octagonal. In both embodiments, preferably the spherical joints are fixed in the table through partially through holes ($h_i$) machined in the lower table surface and the precision manufactured guiding surfaces ($g_3$) through screws. The working diagram of obtaining simple motions, e.g., X and Y translations are the same, in both variants. But for the remaining, they are as the followings: 1) Z motion is coming as—a) four(4) and b) eight(8) and 2) Rx and Ry—a) two (2) and b) eight (8) axes together work (FIG. 5b1) with direct influence on positioning parameters and subsequently, the performances. In addition, the distance (d) between modules are different: a) $d_a$ and b) $d_b$ ($d_a < d_b$), respectively. This means the device in the b) case can be designed with a smaller footprint (compact) or with a larger central aperture (D) for the same footprint for easier cable management as is very often necessary in the diffractometers' environment. By the above design both, the (Pm) component and whole assembly, the parallel positioning table is exhibiting a high degree of modularization and re-configurability; and, with an acceptable cost-effective product because relative few and simple parts are involved.

The way of producing the output motions based on the afferent input motions (or, displacements) is a necessary step to understand the working behavior and to evaluate the capabilities of a new device. The method of basic operational principle is described in FIG. 6. The Rd-PPT device is supposed to be with direct drive (planar motors) in the nominal position (Pn). This means null orientation (Rx=Ry=Rz=0) and displacements for the table center (A; X=Y=0, Z=h) which is corresponding null displacements in the actuation units $Ac_i$ ($B_i$; $X_1=Y_1=0$; $X_2=Y_2=0$; $X_3=Y_3=0$, $X_4=Y_4=0$). The basic motion sequences: a) X, Y, or Rz and b) Rx, Ry and Z imposed to the table are seen in relation with the Actuation modules ($Ac_i$) changes. The final position (Pf) is marked as dash-dot line.

Back and forth translational motions along X axis (Tx) are realized by synchronized motion of all actuators along specified axis and in the same direction ($t_{i1}$, i=1, . . . , 4); the remaining motions-along Y axis ($t_{i2}$, i=1, . . . , 4) being inactivated (or, free), FIG. 6a1. Supposing a positive displacement (X) of point (A) from initial to final (A') position, all the motors related with the same axis must be activated and in the same direction moving with the same values (X=X1=X2=X3=X4); or, at least three of them (the forth could be inactivated on this direction). For example, if Ac1(X1), Ac2(X2) and Ac3(X3) are moving, then Ac4 (X4) could be completely free. The following relations exist: X=X1=X2=X3(=X4); Y1=Y2=Y3=Y4=0.

The same procedure applies to second orthogonal and coplanar axis (Y), FIG. 6a2. Back and forth translational motion along Y axis (Ty) is realized by synchronized translational motions of all actuators along specified axis ($t_{i2}$, i=1, . . . , 4) and in the same direction. Supposing a linear displacement along Y axis of point A(Y), the synchronized motions of all Actuation units ($Ac_i$, i=1, . . . , 4) related with the Y axis must be activated and move in the same direction (Y=Y1=Y2=Y3=Y4); or at least three of them. That means, for example, if $Ac_1$ ($Y_1$), $Ac_2(Y_2)$ and $Ac_3(Y_3)$ are activated and moves; $Ac_4(Y_4)$ can be inactivated: Y=Y1=Y2=Y3(=Y4); X1=X2=X3=X4=0.

Vertical back and forth translational motions (Tz) of the table can be performed by simultaneously concurrent motions of all actuation unit ($Ac_i$, i=1, . . . , 4), FIG. 6b3 or at least three of them. Supposing A point displacement along Z axis (Z), then all the Actuation units (Ac) are activated and pairs move together concurrently in opposite directions towards the Z axis Z=tgα$X_1$=tgα$Y_2$=tgα$X_3$(=tgα$Y_4$) or the point (B)—the base center; or, at least three of them (the corresponding forth one being inactivated). That means, for example, $Ac_1(-X_1)$, $Ac_2$ ($-Y_2$) and $Ac_3$ ($X_3$) are activated and moves, and $A_4(Y_4)$ not.

Symmetric rotations around X or Y axis (Rx or Ry) are achieved by combined back and forth linear motions ($t_{i1(2)}$, i=1,2) of a pair of two actuators $Ac_i$ (i=1,2), or at least one non-collinear with the axis of rotation, FIGS. 6b1 and b2. In order to obtain a positive angular displacement α (β) simultaneously linear displacements actions in opposite directions along the correspondent orthogonal axis must be performed. For example, for Rx(α) imposes $A_2(-Y_2)$ and/or $A_4(-Y_4)$ and for Ry (β) imposes $A_1$ ($X_1$) and $A_3(X_3)$ to work for which α(β)=arctg($Z_i/a_i$), where $Z_i$=$X_i(Y_i)$darctg($α_i$).

Symmetric rotations around the Z axis (Rz) are achieved by combined back and forth linear motions ($t_{i12}$, i=1, . . . , 4) of the entire set of four actuators $Ac_i$ (i=1, . . . , 4), or at least three of them, FIG. 6b3. In order to obtain a positive angular displacement γ simultaneously linear displacement actions in the same direction around the Z axes must be performed. For example, for Rz(γ) imposes $A_1(-X_1, Y_2)$, $A_2(-X_2, -Y_2)$ and $A_3(X_3, -Y_3)$ to work for which γ=arctg $(Y_i/X_i)$.

As resulted from above, by choosing a number of four legs acting and supporting points as a number in-between three points necessary for minimum stability and maximum six imposed for full motion capabilities, and by using compact bi-directional linear actuators, this parallel positioning table is providing a trade-off, between an increased accuracy, speed and stability and dexterity, being able to deliver high power, high-energy efficient 3D positioning trajectories.

The above Redundant Parallel Positioning Table (Rd-PPT) concept can be applied for accurate, high speed, table-like automated or manually driven applications, as for example: alignment, simulation, machining, assembly, measurement, control, or testing or any other operations, from mechanical, optics, semiconductors (lithography, LCD, wafer, printing, etc.) processes in manufacturing, aviation, medical or bio-technological fields including their use in extreme environments (vacuum, cryogenic, magnetic, etc.).

The examples as described above provide a device and method to automatically (or, manually) pose one body or several heavy bodies in space with required precision, speed and stability. The positioning table device is based on symmetric redundant six-degrees-of-freedom spatial parallel kinematic mechanism, a member of the Quadropods family. Each pod (leg) is built as a vertical supporting positioning module actuated by an in-parallel two-degrees-of-freedom motorized unit with motors located at the base and supporting two non-motorized—the elevation and the guiding positioning units, respectively. The elevation units consist from two opposite wedge systems arranged in pairs following the guiding positioning units from spherical bearings types. Through their combined actions, a platform-like table can be easily and intuitively moved in linear and rotational Cartesian directions. In order to manipulate heavy loads as usually in synchrotron applications they are, the device has the characteristics of compact size, low profile, and simple structure providing increased stiffness, precision, and speed positioning capabilities compared with prior art.

The Redundant Parallel Positioning Table (Rd-PPT) device can be adapted to work with fewer than 6 dof. The devices having 2 dof, 3 dof, 4 dof, or 5 dof are derived from the general 6 dof device with appropriate modifications. These modifications provide devices with fewer than 6 dof that have similar performance and comparable capabilities, thereby providing more options for sample/diffractometer positioning.

Further, the present invention provides fast and easy methods to adapt a 6 dof device to various changeable working conditions in the diffractometer environment.

By modifying one or more of the active and/or passive joints from the basic general structure 6-4-213 of FIG. 1 with similar joints having restricted functionalities, located on the first (I), second (II), and/or third (III) levels, as a) active joints—two (2) (2 dof) with $2_1$ (1 dof), b) passive joints—one (1) dof with $1_0$, and c) three (3) dof with $3_2$ (2 dof), $3_1$ (1 dof) or $3_0$ (0 dof) while $_0$—null, $_1$—one, $_2$—two indices are the effective dof permitted for a joint, different modified structures (Sm) can be obtained. Note that in the case of null (0) permitted motions, the joint is (and, the entire level) can be eliminated.

The complete range of Sm structures includes twelve (12) members. For each of these, the redundancy (Rd) changes accordingly.

In the case of when the unmodified active joints (2) are substituted with constrained joints (21), the following structures a) $4-2_113_2$, $4-2_113_1$, $4-2_113_0$ ($2_11$) based on 1 dof passive joints and b) $4-2_11_03_2$ ($2_13_2$), $4-2_11_03_1$, $2_11_03_0$ ($2_1$) for constrained $1_0$ substitute joints are obtained based on the general 6-4-213 structure. Note that only one effective axis can be eliminated from an actuation point.

By modifying/substituting the passive 1 dof joint (1) with a constrained $1_0$ (blocked) joint, in the general case of 6-4-213, the following structures: $4-21_03_2$ ($23_2$), $4-21_03_1$ ($23_1$), $4-21_03_0$ (2) are of interest.

By substituting the 3 dof joints with constrained joints $(3_c)$—$3_2$ and $3_1$ and $3_0$, three Sc structures are obtained by substituting them into the general/unconstrained joints (6-4-213): $4-213_2$, $4-213_1$, and $4-213_0$ (4-21).

Based on the general $6-4-(Pl)_2XS$ mechanisms (6 dof) from FIG. 2 having $(Pl)_2$ generalized curvilinear planar joints/2 dof, X-undefined 1 dof joint, S-spherical joint, a general specific modified mechanism for less than 6 dof (<6)-4-$(Pl)_iX_jS_k$ can be defined. Here, i=1, j=0, k=0,1,2 indices represent the number of effective motions available for the constrained joints in a kinematic modified chain ($K_m$) of a mechanism.

By using the same type of joints (P and S) as in the 6 dof/6-4-(2P)PS mechanism, FIG. 3, the following $M_m$ mechanisms are found that have fewer dof: a) spatial—$5-4-(2P)PS_2$ (5 dof/XYZRxRy), $4-4-(2P)PS_1$ (4 dof/XYZRz), $3-4-(2P)PS_0/3-4-(2P)P$ (3 dof/XYZ) and b) planar $3-4-(2P)P_0S_1/3-4-(2P)S_1$ (3 dof/XYRz) and $2-4-(2P)P_0S_0/2-4-(2P)$ (2 dof/XY); $S_2$ performs 2 dof (Rx,Ry) and $S_1$ (Rz) 1 dof rotational motions only. Note that, by the specificity of the mechanism, the Rz motion is always related to X and/or Y motion (actuation), and Rx and/or Ry with Z motion, respectively.

By using the active constrained joints $(2P)_1$, working mechanisms with fewer dof are: a) 3 (XYZ)-$4-(2P_1)PS_0$ ($3-4-(2P)_1P$) and b) 2 (XY)-$4-(2P)_1P_0S_0$ ($2-4-(2P)_1$); $P_1$ performs linear (1 dof) motion in the actuation. However, in this case, at least four active (effective) axes must work and be concurrent in the same point (base center).

By using the same modular concept as in FIG. 4, including the base, table and positioning modules (Pm) for legs, the design concepts for fewer than 6 dof can use all positioning units (Pu), FIG. 5a and their arrangements FIG. 5b, as in the basic 6 dof concept (Ac-active, El, Gu-passive) or, only some of them, through an adequate modified design, e.g., 3 (XYZ)-4-(2P)P—(Gu), 3(XYRz)-4-(2P) $S_1$—(El). The last two (El and Gu) can be completely eliminated, as in 2 (XY)-4-(2P).

Figure 6:
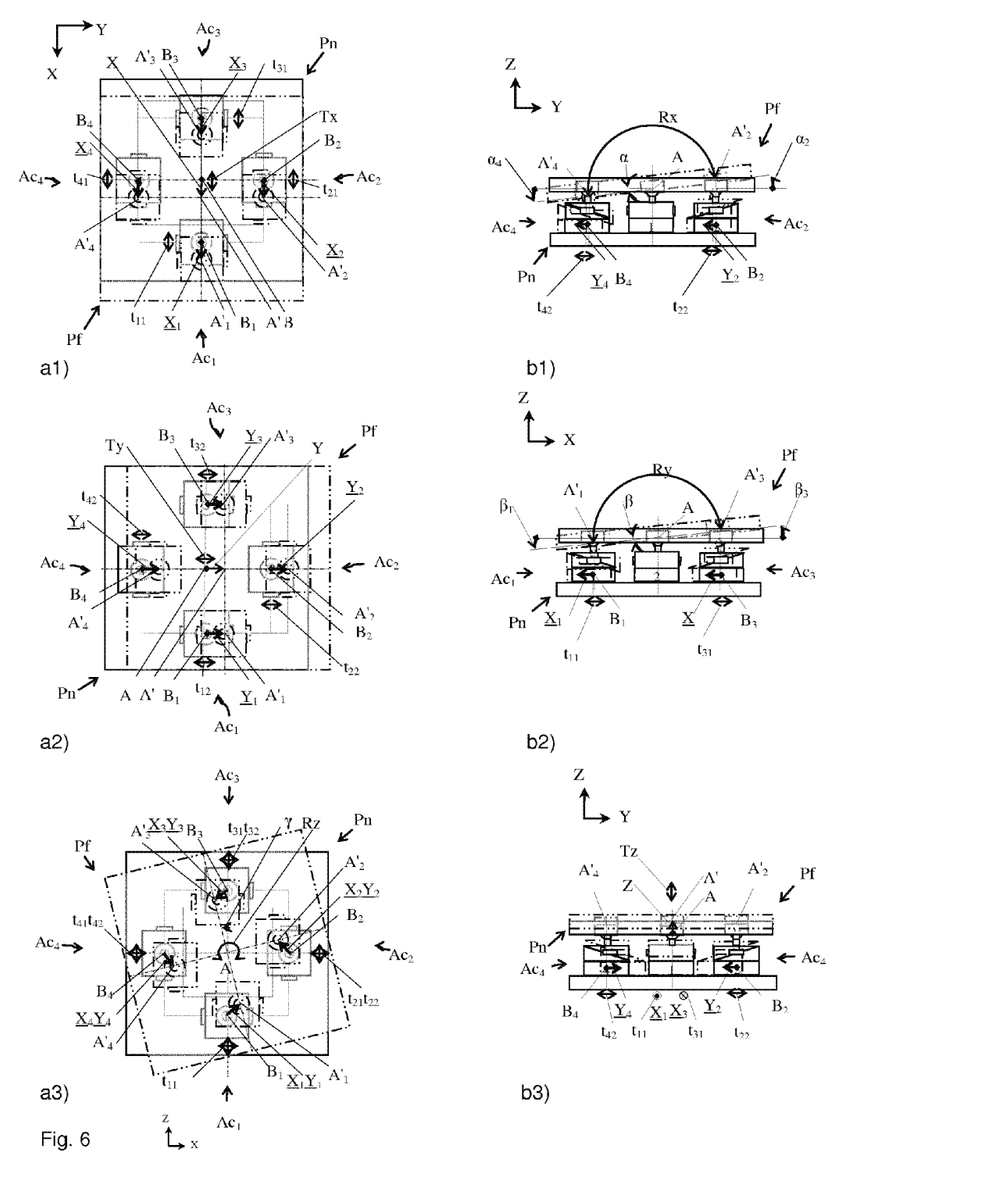
FIG. 6 describes the basic operational principle for the positioning table device.

The methodology to obtain the simple translational (Tx, Ty, Tz) and/or rotational motions (Rx, Ry, Rz) for any of the modified devices above, starting from the nominal position $(X_{ij}=Y_{ij}=0, i=1,2,3,4, j=1,2)$, is, in principle, the same and is derived from the 6 dof device, as in FIG. 6.

By using modified (constrained) dof and two (P and S) types of joints only, several devices with fewer than 6 dof have been produced in addition to those with 6 dof. However, by using all types of joints, different other working devices with fewer than 6 dof can be obtained from the 6 dof device, forming a complete family (213) of redundant parallel positioning table devices. Moreover, by modifying the actuation axes locations, as for example 123, the Quadropods' family of redundant parallel positioning table devices can be enlarged with other members.

When the speed and dynamics of a device are not the main concern, positioning mechanisms having other structures with similar or improved performance can be employed. For example, the present Redundant Parallel Positioning Table (Rd-PPT) device can be adapted to work with increased performance regarding the manipulated sample (load). Such devices are derived from the general 6 dof device by applying suitable modifications.

The present invention provides a device with 6 dof that has features and scope similar to the device taught above but with increased performance, by which more options for sample/diffractometer load manipulation are provided.

Specifically, the invention provides a solution for adapting the device to work in diffractometer environments with an increased load by better transfer of the force from the actuation to the table being more uniformly dispersed inside the components, especially in performing vertical motions. Thus, a greater load can be manipulated without the design modifications as to increase the size (including stiffness) of the components (passive joints) by using the same actuation (power). In other words, a smaller device can perform increased load manipulation with the same passive components.

In this respect, one of the actuation axes of the active joints from the basic structure (6-4-213) of FIG. 1 will become passive and in turn, the next passive joint will become active. With this modification, the newly modified 6-4-123 structure ($S_m$) has the active joint (2) on the second level (II), being able to work with the same number and type of joints as the basic 6 dof device, but with another expected results regarding its positional behavior (load manipulation). In fact, $S_m$ is another member of the larger family of redundant parallel kinematic structures (1,2,3) described above. Note that the other members, 6-4-231/6-4-321 and 6-4-132/6-4-312 are not of interest because, as noted previously, the invention is limited to structures with active joints on levels I and/or II, and spherical joints on level III.

On the basis of the generalized 6-4-(Pl)2XS mechanisms from FIG. 2, having (Pl)$_2$ generalized curvilinear planar joints/2 dof on level I, X-undefined 1 dof joint, S-spherical joint on level III, a generalized modified mechanism $(GM)_m$ 6-4-X(Pl)$_2$S is defined. Here, the (Pl)$_2$ joint on level II can generally perform inclined and horizontal and vertical planar motions ($\Sigma_p$).

By using the same type of joints in a kinematic chain (K), as in the 6-4-(2P)PS mechanism from FIG. 3, but with a modified arrangement, a modified mechanism $M_m$ is defined as 6-4-P(2P)S. Here (2P) represents an in-parallel vertical planar actuation joint, performing horizontal and vertical (inclined) motions. These occur by making one of the active axes of the planar joints (X or Y) and the passive, inclined (α) joint to be active. However, this can also be done in serial (stacked) mode. By this, 6 or fewer dof can be obtained from a synchronized combination of all or fewer actuation axes, e.g., 3(XYZ) with 6-4-P(2P), 3 dof (XYRz) with 6-4-P(2P)S, 2 dof(X/YZ) with 6-4-2P. Note that for fewer dof, some of the joints can be eliminated, e.g., 3(XYZ)—S, 3 dof(XYRz)—P(inclined), 2 dof(XY)—P(inclined) and S.

By using the same modular concept in the design, as exemplified in FIG. 4, including the base, table and positioning modules (Pm) for legs, comprising the same positioning units (Pu)—Ac(actuation), El (Elevation), Gu (Guiding) as in the basic concept, however with partially modified functionalities, a modified redundant parallel kinematic positioning device $(Rd-PPT)_m$ can be produced. This means that the first axes of the Ac positioning module become passive and the El (wedges) positioning module becomes active. This has a beneficial effect in the case of electromechanically actuation (motors and ball screw) the device being able to work with larger inclinations without forcing the horizontal actuation bearing assembly, as a result of the wedge effect. Note that the limited working angle is approximately 30°.

As in the preferred embodiment of the present invention FIG. 5a, a Positioning module (Pm) is a vertical stacked combination of three Pu, one active (Ac)—planar driven (Pu$_1$), and two inactive—El (Pu$_2$) and Gu (Pu$_3$), the first two as generally, compact parallelepiped blocks. However, in the modified design, the $(Ac)_m$ having the first actuation axes inactive (A11), and the second A12 axes still active, the Pu$_2$ becoming active, the detailed design has to be adapted accordingly. The inclined actuation is now acting closer to the table, stressing only the Gu components for up and down vertical motions. And, in the case of motor and ball screw actuation, the motors can be inside or outside, depending on the required aperture, FIG. 5b. Note that the inside variant can restrain the inner available workspace of the device.

The methodology for obtaining the simple translational (Tx, Ty, Tz) and/or rotational motions (Rx, Ry, Rz) for the modified $(Rd-PPT)_m$ device, starting from the nominal position (Xij(Yij)=Zij=0, i=1,2,3,4, j=1,2), remains in principle the same as that of the unmodified device of FIG. 6, however with the specific kinematic values, Tx (X=Xij, i=2,4; j=1), Ty (Y=Yij, i=1,3; j=1), Tz (Z=Zi=Xij(Yij)tg(α), where Xij (Yij)=Li[cos(α)], Li-inclined motion distance, i=1, . . . , 4; j=1,2). Higher Tz(Z) displacements can be obtained by increasing the inclination angle of the wedge to be greater than 30°. And the available height of the working space will also be enlarged. Note that the X/Y displacements again come from the basic combination of Level I (and II) planar axes (active and passive).

By the modifications described above, some performance characteristics of 213 mechanism are improved, and the Quadropods' family of redundant parallel positioning table devices is enlarged by a new member (123). In addition, by using adequate modified (constrained) joints, devices with fewer than 6 dof can be obtained in order to complete the entire portfolio of possible Rd-PPT products.

Thus, it has been shown and described a redundant parallel positioning table device. Since certain changes may be made in the present disclosure without departing from the scope of the present invention, it is intended that all matter described in the foregoing specification and shown in the accompanying drawings be interpreted as illustrative and not in a limiting sense.

The invention claimed is:

1. A redundant parallel positioning table device Rd-PPT comprising:
   (a) a stationary base B;
   (b) a table T with a fixing surface $\Sigma_T$ on which a sample Sp can be mounted;
   (c) at least one set of four supporting legs, one being redundant, the legs arranged around a center of the base symmetrically and in opposed pairs, each leg having a base end connected to the stationary base and a table end connected to the table;
   d) each leg being a 213 kinematics chain K, such that at least one axis of the joints of at least one level are constrained, thereby providing fewer than 6 dof.

2. The redundant parallel positioning table device of claim 1 wherein the parallel positioning table device is modular with the supporting legs as positioning modules Pm, the positioning modules being parallel to each other, vertical with respect to one axis of symmetry Z, and orthogonal with respect to a second axis of symmetry X/Y.

3. The redundant parallel positioning table device of claim 2 wherein the positioning modules Pm are located symmetrically about a central location of the table T.

4. The redundant parallel positioning table device of claim 2 wherein each of the positioning modules comprises a stacked combination of an active planar positioning unit Ac, a passive elevation positioning unit El, and a passive spherical guiding positioning unit Gu.

5. The redundant parallel positioning table device of claim 4 wherein the planar positioning unit Ac includes a base b fixed to the stationary base, a mover M movable relative to the base in two orthogonal axes planar to the base, a linear actuator $A_{11}$ moving the mover M in the first orthogonal axis, a linear guide actuator $A_{12}$ guiding moving the mover M in the second orthogonal axis, a redundant linear actuator $A'_{11}$ moving the mover M in the first orthogonal axis, and a redundant linear guide actuator $A'_{12}$ guiding moving the mover M in the second orthogonal axis.

6. The redundant parallel positioning table device of claim 5 wherein, the first orthogonal axis of a first opposing pair are parallel to each other and the second orthogonal axis of the first opposing pair are parallel to each other, and the first orthogonal axis of a second opposing pair are parallel to each other and the second orthogonal axis of the second opposing pair are parallel to each other forming a planar eight-axis module.

7. The redundant parallel positioning table device of claim 4 wherein, the elevation positioning unit El comprises a pair of wedges $W_{21}$, $W_{22}$ movable relative to each other on V-type inclined guiding surfaces $\Sigma_{21}$, $\Sigma_{22}$, and wherein the lower part $W_{21}$ is fixed to the planar positioning unit Ac and the upper part $W_{22}$ supports the spherical guiding positioning unit Gu, the inclined guiding surfaces of an opposed pair of legs forming a V shape assembly.

8. The redundant parallel positioning table device of claim 4 wherein, the passive spherical guiding positioning unit Gu is a spherical joint S with a truncated conical pillar p mounted to the positioning unit El, a precision sphere S attached to the pillar p and having convex surface $\Sigma_{31}$, a housing $H_1$, $H_2$ having an adjustable concave surface $\Sigma_{32}$ slidable on the convex surface $\Sigma_{31}$, the housing $H_1$, $H_2$ connected to the bottom side of the table.

* * * * *